(12) United States Patent
Baughman et al.

(10) Patent No.: US 9,980,898 B2
(45) Date of Patent: May 29, 2018

(54) POLYMER COMPOSITION FOR HIGH-HEAT APPLICATION COMPRISING THERMO-RELEASABLE SUBSTANCE

(71) Applicant: DSM IP ASSETS B.V., Heerlen (NL)

(72) Inventors: Travis Baughman, Echt (NL); Robin Elisabeth Maria Jacobus Daenen, Echt (NL); Alexander Antonius Marie Stroeks, Echt (NL); Franciscus Johannes Marie Derks, Echt (NL); Pieter Gijsman, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days. days.

(21) Appl. No.: 14/914,205

(22) PCT Filed: Aug. 29, 2014

(86) PCT No.: PCT/EP2014/068348
§ 371 (c)(1),
(2) Date: Feb. 24, 2016

(87) PCT Pub. No.: WO2015/028591
PCT Pub. Date: Mar. 5, 2015

(65) Prior Publication Data
US 2016/0213602 A1    Jul. 28, 2016

(30) Foreign Application Priority Data

Aug. 30, 2013 (EP) .................................... 13182489
Apr. 10, 2014 (EP) .................................... 14164294

(51) Int. Cl.
| | |
|---|---|
| C08K 3/02 | (2006.01) |
| A61K 8/92 | (2006.01) |
| A45D 2/00 | (2006.01) |
| C08L 67/08 | (2006.01) |
| A61Q 5/06 | (2006.01) |
| A45D 19/16 | (2006.01) |
| A61K 8/891 | (2006.01) |
| A61Q 5/12 | (2006.01) |
| C08L 101/12 | (2006.01) |

(52) U.S. Cl.
CPC ............ A61K 8/922 (2013.01); A45D 2/001 (2013.01); A45D 19/16 (2013.01); A61K 8/891 (2013.01); A61Q 5/06 (2013.01); C08L 67/08 (2013.01); A61K 2800/24 (2013.01); A61K 2800/805 (2013.01); A61Q 5/12 (2013.01); C08L 101/12 (2013.01)

(58) Field of Classification Search
None
See application file for complete search history.

(56) References Cited

U.S. PATENT DOCUMENTS

| | | | | |
|---|---|---|---|---|
| 4,867,881 | A * | 9/1989 | Kinzer | .............. A61F 13/00008 |
| | | | | 210/490 |
| 2003/0105273 | A1* | 6/2003 | Appelman | ........... C08G 63/199 |
| | | | | 528/272 |
| 2010/0163071 | A1* | 7/2010 | Everett, Jr. | .............. A45D 1/04 |
| | | | | 132/223 |
| 2013/0059246 | A1 | 3/2013 | Hong | |
| 2013/0115183 | A1* | 5/2013 | Ko | ......................... A61Q 5/006 |
| | | | | 424/70.11 |

FOREIGN PATENT DOCUMENTS

| | | |
|---|---|---|
| EP | 2 204 104 | 7/2010 |
| JP | 2004-269899 | 9/2004 |
| WO | WO 2011/141878 | 11/2011 |

OTHER PUBLICATIONS

International Search Report and Written Opinion of the ISA for PCT/EP2014/068348, dated Nov. 27, 2014, 10 pages.
J.Bicerano, Prediction of Polymer Properties, Marcel Dekker, 3rd Ed, 2002, ISBN 0-8247-0821-0, Chapter 5.

* cited by examiner

Primary Examiner — Robert T Butcher
(74) Attorney, Agent, or Firm — Nixon & Vanderhye P.C.

(57) ABSTRACT

The invention relates to a polymer composition suitable for high-heat application comprising: a. At least one polymer 1 having a solubility parameter $\delta P1$; b. A thermo-releasable substance being a liquid at 200° C. and having a solubility parameter $\delta sub$ in an amount of at least 0.1 wt % with respect to the total amount of composition; and wherein the amount of thermo-releasable substance is in the range from 0.5 wt % to 70 wt % with respect to the polymer 1; wherein $\Delta = (\delta sub - \delta P1)^2$ is in the range from 0.5 to 24.0 and wherein the solubility parameter is calculated by the software package Synthia, Materials Studio v.6.0.0 ©2011, based on the method by J. Bicerano, Prediction of Polymer Properties, Marcel Dekker, 3rd Ed, 2002, ISBN 0-8247-0821-0; Chapter 5, and in which the E-modulus of the composition as measured according to method ISO 527-1 at 200° C. is at least 50 MPa. The invention also relates to personal care devices and hair-straighteners comprising this polymer composition.

17 Claims, No Drawings

POLYMER COMPOSITION FOR HIGH-HEAT APPLICATION COMPRISING THERMO-RELEASABLE SUBSTANCE

This application is the U.S. national phase of International Application No. PCT/EP2014/068348 filed 29 Aug. 2014, which designated the U.S. and claims priority to EP Patent Application No. 13182489.8 filed 30 Aug. 2013, and EP Patent Application No. 14164294.2 filed 10 Apr. 2014, the entire contents of each of which are hereby incorporated by reference.

This invention relates to a polymer composition suitable for high heat application which comprises at least one polymer and a thermo-releasable substance.

Polymer compositions comprising at least one polymer and a thermo-releasable substance are known and are for example disclosed in EP2204104. EP2204104 discloses a personal care device comprising an immiscible conditioning composition of a hydrophobic conditioning agent and a hydrophilic material, wherein the hydrophobic conditioning agent is a fluid and the hydrophilic material is a porous solid.

A drawback of the composition as disclosed in EP2204104 is that not enough release of the conditioning agent is observed on hair after application, especially for applications at higher temperatures.

It is thus an object of the present invention to provide compositions which exhibit higher release upon application at high-heat.

This has surprisingly been accomplished by a polymer composition suitable for high-heat application comprising:
  a. At least one polymer 1 having a solubility parameter $\delta P1$;
  b. A thermo-releasable substance being a liquid at 200° C. and having a solubility parameter $\delta sub$ in an amount of at least 0.1 wt % with respect to the total amount of composition; and wherein the amount of thermo-releasable substance is in the range from 0.5 wt % to 70 wt % with respect to the polymer 1;
wherein $\Delta=(\delta sub-\delta P1)^2$ is in the range from 0.5 to 24.0 and wherein the solubility parameter is calculated by the software package Synthia, Materials Studio v.6.0.0 ©2011, based on the method by J. Bicerano, Prediction of Polymer Properties, Marcel Dekker, 3rd Ed, 2002, ISBN 0-8247-0821-0; Chapter 5, and in which the E-modulus of the composition as measured according to method ISO 527-1 at 200° C. is at least 50 MPa.

The polymer composition exhibits higher release of the thermo-releasable substance, which is exemplified by the examples below. Moreover, also the mechanical strength is sufficient, especially for applications at higher temperatures.

With high-heat application in the current invention is meant, application at temperatures of at least 100° C., also referred to as application temperature. Preferably, the applications are employed at a temperature of at least 150° C., more preferably at least 170° C. and most preferred at least 190° C. An upper limit for the temperature for these applications usually is at most 240° C., preferably at most 230° C. and most preferred at most 220° C.

Polymer 1

Polymer 1 can be any polymer with solubility $\delta P1$. Such polymers include thermoplastic polyesters, syndiotactic polystyrenes like SPS 142ZE, SPS 300ZC and SPS 90ZC, styrene maleic anhydride copolymers like SMA SZ08250, polybutylenenaphthalate (PBN), polyethylenenaphthalate (PEN), polyethyleneterephthalate (PET), polybutyleneterephthalate (PBT) as well as polyamides.

Thermoplastic polyesters include polybutyleneterephthalate-co-dimerfattyacid, known as PBT 20% DFA, PBT 40% DFA, ArnitelEL740, in which DFA stands for dimerized fatty acids and amounts in weight percentage that are added as co-monomer during the polymerization of polybutyleneterephthalate. Suitable dimerized fatty acids include:

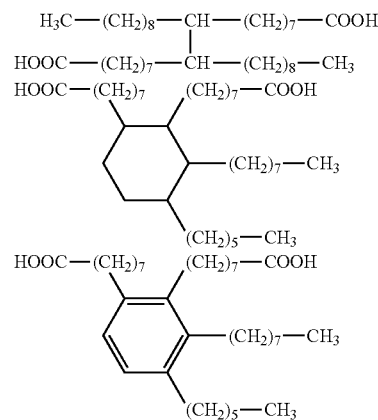

The composition according to the invention can comprise more than one polymer. A further polymer, hereafter also referred to as polymer 2, polymer 3, etc, may for example be present to increase mechanical properties. Suitable further polymers include semi-crystalline polymers with a melting temperature of at least 10° C. above the application temperature, such as PET, polyamides, polystyrenes, PBN and PEN. Suitable further polymers also include amorphous polymers with a glass transition temperature of at least 10° C. above the application temperature.

If multiple polymers are present in the composition, polymer 1 is defined as the polymer for which the absolute difference of the solubility parameter of the thermo-releasable substance and the polymer is the smallest. The solubility parameter of polymer 2 is hereafter referred to as $\delta P2$.

Thermo-Releasable Substance

A thermo-releasable substance according to the invention is a substance that is liquid at 200° C. at atmospheric pressure. Preferably the thermo-releasable substance has a steady shear viscosity in the range from 0.1 mPas to 1000 mPas at 200° C. at atmospheric pressure and more preferably the steady shear viscosity is in the range from 0.1 mPas to 500 mPas at 200° C. at atmospheric pressure.

The steady shear viscosity is measured by means of a shear rate sweep experiment, which method is known to a person skilled in the art. This type of experiment uses a cylinder which rotates in a cup, a so-called double gap spindle, filled with the specific liquid and can be can be performed on a Physica MCR501 rheometer from Anton Paar. In the gap between cylinder and cup the actual shear rate is achieved. The resulting torque is measured by a transducer connected to the cylinder and recalculated to a shear stress.

A thermo-releasable substance is preferably a hair-care ingredient, which are known to a person skilled in the art. More preferably, the thermo-releasable substance comprises an oil.

Suitable oils include paraffinic oils, both linear and branched. Also suitable are natural oils, such as triglycerides, including argan oil, avocado oil, moringa oil, camealia oil, sunflower oil macadamia nut oil, safflower oil and apricot kernel oil. Also included are waxes such as jojoba oil and sperm oil. Suitable are also non-vegetable oils such as siloxanes, including PDMS, as well as other personal care substances as known in the industry. These include for example ceramide-like compounds (RepHair of Solabia or ceramide II of Givaudan) or other personal care substance like Bis-Ethyl(isostearylimidazoline) Isostearamide (Kera-Dyn HH of Croda). Preferably, the thermo-releasable substance comprises a natural oil, such as avocado oil, argan oil, camealia oil, sunflower oil, macadamia nut oil, safflower oil, apricot kernel oil or combinations thereof.

In case the composition comprises more than one thermo-releasable substance, δsub is defined as the weight average of the δ's of the individual thermo-releasable substances.

Preferred Combinations

Preferably, polymer 1 is chosen from the group consisting of polybutyleneterephthalate-co-dimerfattyacids with the thermo-releasable substance being a natural oil chosen from the group consisting of avocado oil, argan oil, camealia oil, sunflower oil, macadamia nut oil, safflower oil, apricot kernel oil and combinations thereof. More preferably, the composition according to the invention comprises polybutyleneterephthalate-co-dimerfattyacid as polymer 1 and polyethyleneterephthalate (PET) as a further polymer.

Even more preferred the composition according to the invention comprises polymer 1 being a polybutyleneterephthalate-co-dimerfattyacid and the thermo-releasable substance comprises a natural oil chosen from the group consisting of avocado oil, argan oil, camealia oil, sunflower oil, macadamia nut oil, safflower oil, apricot kernel oil and combinations thereof and a further polymer is polyethyleneterephthalate.

Other Additives

The composition according to the invention may optionally comprise any auxiliary additives. Such additives include fillers; pigments; thermo-conductive additives; dispersing aids; processing aids for example lubricants, mould release agents, flow additives; impact modifiers; plasticizers; crystallization accelerating agents; nucleating agents; flame retardants; UV stabilizers; antioxidants; vitamins; heat stabilizers. The polymer composition may optionally comprise fragrances.

Such additives include, in particular, reinforcing fillers. The fillers that may be used as additives to the polymer composition include inorganic fillers. Suitable for use as inorganic fillers are all the fillers, such as reinforcing and extending fillers, known to a person skilled in the art, for example asbestos, mica, clay, calcinated clay, talcum, silicates such as wollastonite, and silicon dioxide, especially glass fibres.

Applications

The polymer composition according to the invention can suitably be processed into a personal care device. It has been shown that the composition according to the invention exhibits good release of thermo-releasable substance in applications at higher temperatures. Perferably, the personal care device comprises a surface for contacting hair, in which the surface is made from the polymer composition according to the invention. A personal care device is preferably heavy metal-free, as heavy metals are considered toxic for humans. Preferably, the personal care does not contain harmful substances as known to be harmful for human hair.

The polymer composition according to the invention can suitably be applied in personal care devices, including hair straighteners, hair blowers, ironing plates. Preferably, the polymer composition is processed into a hair straightener, wherein the thermo-releasable substance is a hair care ingredient having a steady shear viscosity in the range from 0.1 mPas to 1000 mPas at 200° C.

Sleeve

The polymer composition can be extruded and molded in for example sleeves for a straightening device. With sleeve, the contact area for the good-to-be-straightened is meant. The good-to-be-straightened is referred to as subject. The sleeve may be replaceable, which allows for optimum release of the thermo-releasable substance, as after a number of uses, the sleeve can be replaced by a new one.

A sleeve can be attached permanently to the straightener or the sleeve can be replaceable. The advantage of being replaceable is that the consumer can replace the sleeve after a number of uses, which allows for better oil release during time. The straightening device can be designed for subjects such as hair or other goods, such as clothing.

The sleeve can be made partly from the polymer composition according to the invention. This allows optimum function in view of release of the thermo-releasable substance from the polymer composition according to the invention, as well as mechanical performance coming from the remainder of the sleeve. Preferably, the remainder of the sleeve is made from a polymer composition comprising additionally a thermo conductive additive. This allows for good release properties while the subject is less damaged by heat.

Preferably, the polymer composition is processed into sleeves for a hair straightening device as this provides release to hair.

Solubility Parameter

The solubility parameter is a well-known parameter for substances and provides a numerical estimate of the degree of non-covalent interaction within the substance. The unit for the solubility parameter is $\mathrm{sqrt}(J/cm^3)$. The solubility parameter can be assessed experimentally. For low molar mass substances quantification of e.g. enthalpy of evaporation in combination with molar volume gives the solubility parameter. For polymers, however, this method does not work because of their non-volatility. For polymers other more indirect experimental methods can be used to quantify the solubility parameter. One of these methods is solvency testing. With solvency testing a polymer is exposed to a range of different solvents varying in polarity and determining the miscibility. This method is costly and cumbersome.

To circumvent extensive experimental testing, models have been developed to calculate solubility parameters. As input the chemical structure of the polymer or the low molar mass species is used.

In the context of the present invention, the solubility parameter is defined as calculated by the software package Synthia, Materials Studio v.6.0.0 ©2011, based on the method developed by Bicerano as described in J. Bicerano, Prediction of Polymer Properties, Marcel Dekker, 3rd Ed, 2002, ISBN 0-8247-0821-0, Chapter 5. Exemplary solubility parameters (van Krevelen method on page 119) can be found in Table 5.2 last column δ2, on pages 127 to 130 in J. Bicerano, Prediction of Polymer Properties, Marcel Dekker, 3rd Ed, 2002, ISBN 0-8247-0821-0, Chapter 5. For non-listed substances, the solubility parameter (van Krevelen) is calculated by using the software package Materials Studio v.6.0.0 ©2011 module Synthia, which employs the Bicerano method. The solubility parameter (SP) of various polymers can thus be found in the library of the calculation module of Synthia, by selecting the polymers of choice their can SP be calculated. For various common copolymers the SP can be calculated with the same calculation module by selection the monomers of choice and defining the mass or molar fraction of each monomer. The SP of other polymers is calculated by drawing the repeat unit and next selecting build polymer repeat unit and defining a head and tail atom followed by selecting calculate. The SP of oils and other cosmetic ingredients is calculated by drawing the structure of the oil and next selecting build polymer repeat unit and defining a head and tail atom as if the structure was a monomer unit, followed by selecting calculate.

For common thermo-releasable substances the solubility parameter according to the Bicerano method is given in the table below, as calculated by Synthia program, as well as common polymers. Natural oils usually consist of a blend of several fatty acids, which is taken into account for calculation of the solubility parameter. First the solubility parameter of various pure triglycerides with the 3 same fatty acids was calculated (left part table 2). Next the solubility parameter of the natural oil was calculated based on the weight fraction of the individual triglycerides (right part table 2).

TABLE 1 solubility parameter various thermo-releasable substances and polymers

| | Van Krevelen solubility parameter $(J/cm^3)^{1/2}$ |
|---|---|
| Thermo-releasable substance (sub) | |
| PDMS (Polydimethylsiloxane) | 14.2 |
| Parsol SLX (Polysilicone-15) | 15.4 |
| Phenyltrimethicone | 15.7 |
| Squalane | 16.4 |
| Linear parafine | 16.8 |
| Jojoba Oil | 17.0 |
| Isopropyl Palmitate | 17.0 |
| Isopropyl Myristate | 17.0 |
| Keradyn HH | 17.8 |
| RepHair | 19.6 |
| Octyldodecanol | 19.7 |
| Cholesterol | 19.9 |
| Ceramide II | 21.8 |
| Polymers: | |
| polydimethylsiloxane | 14.2 |
| polyethylene | 16.8 |
| polypropylene | 16.1 |
| polyisobutene | 15.4 |
| polystyrene | 19.5 |
| polymethyl styrene | 18.7 |
| polymethylacrylate | 18.6 |
| polypropylacrylate | 17.6 |
| polymethylmethacrylate | 17.7 |
| polypropylmethacrylate | 17.1 |
| polyvinyl chloride | 19.6 |
| polyacrylonitrile | 24.6 |
| polyoxymethylene | 20.6 |
| polyethyleneoxide | 19.1 |
| polypropyleneoxide | 17.6 |
| polytetramethylene oxide | 18.1 |
| polybutyleneterepthalate (PBT) | 19.3 |
| polyethyleneterepthalate (PET) | 19.8 |
| nylon 12 | 21.5 |
| nylon 6 | 25.1 |
| nylon 66 | 25.1 |

TABLE 2 solubility parameter calculation natural oils

| fatty acid: | C-atoms (number of double bonds) | δ in $(J/cm^3)^{1/2}$ triglyceride | Argan Wt fraction | Avocado Wt fraction | Sunflower Wt fraction | Camelia Wt fraction | Macadamia Wt fraction | Safflower Wt fraction | Apricot kernel Wt fraction |
|---|---|---|---|---|---|---|---|---|---|
| myristic | 14 | 17.17 | | | | | 0.01 | | |
| palmitic | 16 | 17.13 | 0.13 | 0.18 | 0.11 | 0.06 | 0.09 | 0.06 | 0.06 |
| palmitoleic | 16 (1) | 17.34 | | 0.04 | | | 0.19 | | 0.01 |
| stearic | 18 | 17.10 | 0.05 | 0.02 | 0.06 | 0.02 | 0.04 | 0.02 | 0.02 |
| oleic | 18 (1) | 17.28 | 0.47 | 0.63 | 0.29 | 0.84 | 0.59 | 0.77 | 0.61 |
| linoleic | 18 (2) | 17.46 | 0.00 | 0.12 | 0.54 | 0.077 | 0.03 | 0.14 | 0.29 |
| linolenic | 18 (3) | 17.67 | 0.35 | 0.01 | 0.00 | 0.003 | 0.00 | 0.01 | 0.01 |
| eicosanoic | 20 | 17.07 | | 0.002 | | | 0.03 | | |
| eicosenoic | 20 (1) | 17.24 | | | | | 0.02 | | |
| | | δ in $(J/cm^3)^{1/2}$ oil | 17.4 | 17.3 | 17.4 | 17.3 | 17.1 | 17.3 | 17.3 |

It has surprisingly been bound that a good release has been observed if the following formula is true:

$\Delta = (\delta_{sub} - \delta P1)^2$ is in the range from 0.5 to 24.0

The inventors have observed that in a polymer composition in which $\Delta$ is above 24.0, for example in immiscible compositions as disclosed in EP2204104A1, the release of conditioning agent was not sufficient, which is exemplified by the Comparative Examples C_1 to C_3. Also for polymer compositions in which $\Delta$ is very small, e.g. below 0.5, no release of thermo-releasable substance was observed.

Surprisingly, good release was observed if $\Delta$ is in the range from 0.5 to 24.0, preferably $\Delta$ is in the range from 1.0 to 20.0, more preferably $\Delta$ is in the range from 1.0 to 15.0 and most preferred $\Delta$ is in the range from 1.0 to 10.0.

Modulus

The E-modulus of the composition according to the invention is at least 50 MPa as measured according to test method ISO 527-1 at 200° C., as this ensures proper application at high heat. More preferably, the modulus is at least 70 MPa, even more preferably at least 90 MPa, and most preferred at least 100 MPa. The upperlimit for the modulus of the composition can be as high as 5000 MPa, at 200° C. The E-modulus is determined according to test method ISO 527-1 (TENSILE PROPERTIES OF PLASTICS) on test bars prepared according to ISO 527-1A.

EXAMPLES

Materials Used
Polymers:
PA-6=polyamide-6=Akulon K125 or Akulon K122 of DSM
PA-66=polyamide-6,6=S222 of DSM
PA-4,10=polyamide-4,10=EcoPaxx Q150MS of DSM
SPS=Syndiotactic Polystyrene (Idemitsu Chemicals Europe, Xarec 90ZC, Xarec 300ZC, Xarec 142ZE)
PET (A02 36)=polyethyleneterephthalate=Arnite® A02 306 of DSM
PET (5018)=polyethyleneterephthalate=Arnite® BAGA 5018 of DSM
PBT=polybutyleneterephthalate=Arnite® T04 200 of DSM
PBT-Eco=polybutyleneterephthalate-co-dimerfattyacid 20% DFA of DSM (Melt volume rate=3)
PBT-Eco-2=polybutyleneterephthalate-co-dimerfattyacid 20% DFA of DSM (Melt volume rate=25)
PBT-Eco-3=polybutyleneterephthalate-co-dimerfattyacid 40% DFA of DSM (Melt volume rate=40)
PBT-E=polybutyleneterephthalate-co-polytetramethyleneoxide=Arnitel® EL740 (Melt volume rate=15)
PE-MA=Maleic Anhydride Modified Ethylene-Alpha Olefin Copolymer=Bondyram® 7103 of Polyram
SMA 08250=styrenemaleicanhydride copolymer=XIRAN® SZ 08250 of Polyscope Polymers B.V.
PBN-D=polybutylenenaphthanate-co-dimerfattyacid amide=experimental product of DSM
PC=polycarbonate=Xantar 19R of DSM
SAN 581=Poly(styrene-co-acrylonitrile) (75 wt % styrene and 25 wt % acrylonitrile) of Sabic.
Comp=Compatibilizer for PA with SPS: acid modified poly (phenylene ether) CX-1, FA-PPE (Idemitsu Kosan Co., Ltd)
Thermo-Releasable Substances (Abbreviated Sub):
Argan Oil=product code 50 3808 1 of DSM Nutritional Products
Avocado oil=*Persea Gratissima* oil, Avoaodo oil RBD, code 266554 of IMCD
Sunflower oil=product code 1665N of Volatile
Camealia Oleifera Seed Oil=Cropure Yuchayu-LQ-(JP), product code SV70391 of Croda
Jojoba oil=*Simmondsia* Chenensis Seed Oil=Cropure Jojoba of Croda
Macadamia nut oil CPRBD, code 266526 of IMCD
Safflower oil RBDW, code 266969 of IMCD
Apricot Kernel oil RBDW, code 266559 of IMCD
Other Additives:
I-1076=stabilizer Irganox1076 of Ciba (BASF)
Glass=3B CS173-x11 of Owens Corning
Carbon 1)=Expanded Graphite (C-Therm 01)
Carbon 2)=99.25% Expanded Graphite (C-Therm 01) and 0.75% Carbon Black (Black pearls 800)
Carbon 3)=Expanded Graphite (Ecophit GFG1200)
Carbon 4)=95% Graphite (Ecophit GFG1200) and 5% Carbon black (Timcal Ensaco260G)
Abbreviations:
bdl=below detection limit
nd=not determined
Preparing Compositions Various compositions were made according to the tables below. The compositions were compounded on twin screw extruders like ZSK30/44D at a processing temperature being at least equal to the highest of Tg or Tm of the polymer of the composition. After the mixing the hot polymer composition string was cooled in a water bath or cooling belt and cut into granules suitable for injection molding.

Injection Molding

Injection molding was performed at an Engel 110, a machine with 110 ton maximum clamping force with a screw diameter of 30 mm. On this machine 120×120×1 mm³ plates were produced of almost all compositions using plate 120×120×1 mm³, for some materials also mechanical test bars were produced on the Engel 110, for these test bars plate ISO 527-1A pr.80*10*4 2v. was used. From the plates plaques were cut to determine the release of the thermo-releasable substance from the composition when used on the straightener. Test bars (dog-bone) were used to produce stress-strain curves of various compositions.

Thermal Stability of Polymer Plaque

In order to determine the thermal stability of the plaque it was fixed to a straightener and set at 200° C. When no visual melting or deformation of the plaque was observed within about 10 minutes the stability was judged as OK, and these compositions are considered suitable for high-heat application.

Qualitative Release Inspection

In order to judge qualitatively whether a plaque of exhibited release of the thermo-releasable substance at higher temperature, the plaques were fixed to a straightener and set at 200° C. After 5 min it was visually inspected if release of thermo-releasable substance was visible. Qualitative release was present when drops of thermo-releasable substance were visual or could be detected by wiping with fingers.

Quantitative Release Inspection:

In order to quantify the release of the thermo-releasable substance from the plate to hair, the following test method was used.

The test was performed on two injection molded plates of 30×90×1 mm. The two plates were attached to heating plates of a Philips straightener HP 8339 with Kapton tape, to allow maximum contact surface between the plate and the heating plates of the straighteners. The straightener was heated to 200° C. Hair swatches were used as test material being 1.5 cm wide, 23 cm free length held together with by a glued part which was not pulled through the straightener (Klebetresse dicht aus Euro-Natur-Haar, remis, Farbe 6/0, Kerling International Haarfabrik GmbH, item number 826500). The hair swatch was pulled 10 times through the straightener in approximately 10 seconds per pull after which the straightener was kept on and a 15 minutes pause was applied without the hair being in proximity of the straightener. This procedure was repeated twice, thus resulting in a single hair swatch being pulled through the straightener 30 times. During the last pull, the swatch was twisted and put in a flask after cutting off the glued part of the swatch.

4 ml THF (Tetrahydrofuran VWR, chromanorm, prod. code 28559.320) was added to the flask with the swatch and the flask was closed and put on rollers for 15 minutes to allow extraction of the oil from the hair swatch. After these 15 minutes, 1 ml THF/oil mixture was put in a GPC vial for injection on GPC.

GPC Setup

Waters HPLC pump type 515 (flow 1.0 ml/min)
Waters autosampler 717plus (injection volume was set at 100 μl)
Waters column oven, temperature was set to 50° C.
Column set: 2 PL-gel Mixed E-columns from PSS
Differential Refractive Index detector, Waters 2414
System was controlled by software of Waters, Empower. Calibration for determination of released thermo-releasable substance was done by injection of known amounts of thermo-releasable substance. The detection limit for the thermo-releasable substance on hair determination method is 0.08 mg oil/4 ml THF.

The resulting chromatogram was integrated and compared to a calibration curve of the same thermo-releasable substance mixture resulting in an amount of released thermo-releasable substance in mg from two plates to the hair swatch (1,5 cm wide, 23 cm long hair swatch).

This procedure constituted one treatment. This treatment was repeated and release of thermo-releasable substance was measured during treatment no 5 and treatment no 10. The data are shown in the tables below.

TABLE 3

Experiments with various thermo-releasable substances

| Experiment no | sub | sub wt % on total | sub wt % on P1 | $\delta$sub (J/cm$^3$)$^{1/2}$ | Polymer 1 | wt % on total | $\delta$P1 (J/cm$^3$)$^{1/2}$ | Polymer 2 | wt % on total | $\delta$P2 (J/cm$^3$)$^{1/2}$ | Comp wt % | I-1076 wt % | ($\delta$sub − $\delta$P1)$^2$ (J/cm$^3$) | visual sub on plaque | Release at 200° C. [mg] 1st treatment | 5th treatment |
|---|---|---|---|---|---|---|---|---|---|---|---|---|---|---|---|---|
| 1 | Sunflower | 20.1 | 41.8 | 17.4 | SPS (90ZC) | 28 | 19.52 | PA-4, 10 | 48 | 24.2 | 2.9 | 1.0 | 4.7 | yes | 29 | 0.9 |
| 2 | Avocado | 20.1 | 41.8 | 17.3 | SPS (90ZC) | 28 | 19.52 | PA-4, 10 | 48 | 24.2 | 2.9 | 1.0 | 5.0 | yes | 25 | 2.5 |
| 3 | Argan | 20.1 | 41.8 | 17.4 | SPS (90ZC) | 28 | 19.52 | PA-4, 10 | 48 | 24.2 | 2.9 | 1.0 | 4.5 | yes | 25 | 0.7 |
| 4 | Jojoba | 20.1 | 41.8 | 17.0 | SPS (90ZC) | 28 | 19.52 | PA-4, 10 | 48 | 24.2 | 2.9 | 1.0 | 6.2 | yes | 1) | 1) |
| C_1 | Argan | 10 | 10.1 | 17.4 | PA-6 (K125) | 89 | 25.14 | | | | | 1.0 | 60 | no | 0.1 | bdl |
| C_2 | PDMS | 2 | 2.0 | 14.2 | PA-6 (K122) | 98 | 25.14 | | | | | | 120 | no | 2) | nd |
| C_3 | PDMS | 0.5 | 0.5 | 14.2 | PA-66 (S222) | 99.5 | 25.14 | | | | | | 120 | no | 2) | nd |

1) = Quantitative analytical method (GPC) not adequate for this oil but after heating oil was visival on polymer sleeve
2) = Quantitative analytical method (GPC) not adequate for this oil but after heating no oil was visual at polymer sleeve, IR analysis of sleeve was inconclusive

TABLE 4

Experiments with one polymer

| Experiment no | Sub = Argan oil $\delta$ = 17.4 wt % | Polymer 1 | wt % | $\delta$P1 (J/cm$^3$)$^{1/2}$ | I-1076 wt % | ($\delta$sub − $\delta$P1)$^2$ (J/cm$^3$) | Release at 200° C. [mg] 1st treatment | 5th treatment | 10th treatment | thermal stability at 200° C. |
|---|---|---|---|---|---|---|---|---|---|---|
| 5 | 5 | PBN-D | 94.0 | 19.6 | 1.0 | 4.7 | 0.81 | 0.20 | 0.14 | Yes |
| 6 | 17 | SPS (142ZE) | 82.0 | 19.5 | 1.0 | 4.5 | 6.40 | 0.80 | 0.70 | Yes |
| 7 | 29 | SPS (142ZE) | 70.0 | 19.5 | 1.0 | 4.5 | 12.40 | 0.80 | 0.10 | Yes |
| 8 | 29 | SPS (330ZC) | 70.0 | 19.5 | 1.0 | 4.5 | 7.10 | 0.70 | 0.10 | Yes |
| 9 | 29 | SPS (90ZC) | 70.0 | 19.5 | 1.0 | 4.5 | 13.20 | 1.60 | 0.30 | Yes |
| C_4 | 7.5 | PA-4, 10 | 91.5 | 24.2 | 1.0 | 46.2 | bdl | bdl | nd | Yes |
| C_5 | 15 | PBT-Eco | 84.0 | 18.8 | 1.0 | 1.8 | 0.80 | nd | nd | No |

TABLE 5

Experiments with two polymers

| Experiment no | Sub = Argan oil δ = 17.4 wt % | sub wt % on P1 | P1 polymer 1 | P1 wt % on total | δP1 (J/cm³)^(1/2) | P2 polymer 2 | P2 wt % on total | δP2 (J/cm³)^(1/2) | Comp wt % | I-1076 wt % | (δsub − δP1)² (J/cm³) | Release at 200° C. [mg] 1st treatment | 5th treatment | 10th treatment |
|---|---|---|---|---|---|---|---|---|---|---|---|---|---|---|
| 10 | 7 | 17.5 | PBT-Eco | 33.0 | 18.8 | PBT | 59 | 18.8 | | 1.0 | 1.8 | 0.5 | 0.1 | 0.1 |
| 11 | 1.5 | 5.0 | PBT-E | 28.5 | 19.2 | PET | 69 | 19.8 | | 1.0 | 3.3 | nd | 0.2 | 0.1 |
| 12 | 9 | 33.3 | SMA (08250) | 18.0 | 19.9 | PA-4, 10 | 72 | 24.2 | | 1.0 | 6.4 | 0.2 | 0.2 | 0.1 |
| 13 | 22 | 44.0 | SPS (142ZE) | 28.0 | 19.5 | PA-4, 10 | 46 | 24.2 | 3.0 | 1.0 | 4.5 | 12.5 | 1.6 | 0.6 |
| 14 | 21 | 42.0 | SPS (90ZC) | 29.0 | 19.5 | PA-4, 10 | 46 | 24.2 | 3.0 | 1.0 | 4.5 | 20.5 | 3.4 | 0.7 |
| 15 | 10 | 35.7 | SAN (581) | 18.0 | 20.8 | PA-4, 10 | 71 | 24.2 | | 1.0 | 11.6 | 0.7 | 0.1 | nd |
| 16 | 8 | 18.2 | PBT-Eco | 36.0 | 18.8 | PA-4, 10 | 55 | 24.2 | | 1.0 | 1.8 | 0.7 | 0.5 | nd |
| 17 | 8 | 29.6 | PC (19R) | 19.0 | 19.3 | PA-4, 10 | 72 | 24.2 | | 1.0 | 3.7 | 0.3 | nd | nd |
| C_6 | 15 | 46.9 | PE-MA (7103) | 17.0 | 17.3 | PA-4, 10 | 67 | 24.2 | | 1.0 | 0.0 | bdl | nd | nd |

TABLE 6

Experiments with two polymers and quantification of E-modulus

| Experiment no | Sub | sub wt % on total | Sub wt % on P1 | δsub (J/cm³)^(1/2) | Polymer 1 | P1 wt % on total | δP1 (J/cm³)^(1/2) | Polymer 2 | P2 wt % on total | δP2 (J/cm³)^(1/2) | Comp. wt % | I1076 wt % |
|---|---|---|---|---|---|---|---|---|---|---|---|---|
| 18 | Argan | 10.6 | 28.2 | 17.4 | SPS(142ZE) | 27.0 | 19.5 | PA-4, 10 | 44.1 | 24.2 | 2.5 | 0.9 |
| 19 | Argan | 10.6 | 28.2 | 17.4 | SPS(142ZE) | 27.0 | 19.5 | PA-4, 10 | 44.1 | 24.2 | 2.5 | 0.9 |
| 20 | Argan | 8.5 | 28.2 | 17.4 | SPS(142ZE) | 21.6 | 19.5 | PA-4, 10 | 35.4 | 24.2 | 2 | 0.7 |
| 21 | Argan | 8.5 | 28.2 | 17.4 | SPS(142ZE) | 21.6 | 19.5 | PA-4, 10 | 35.4 | 24.2 | 2 | 0.7 |
| 22 | Argan | 5.4 | 15.1 | 17.4 | PBT-Eco | 30.3 | 18.8 | PBT | 53.5 | 19.3 | 0 | 0.8 |
| 23 | Avocado | 4.7 | 14.9 | 17.3 | PBT-Eco | 26.8 | 18.8 | PET (5018) | 47.3 | 19.8 | 0 | 0.8 |
| 24 | Avocado | 7.8 | 20.7 | 17.3 | PBT-Eco | 29.9 | 18.8 | PET (5018) | 43.0 | 19.8 | 0 | 0.8 |
| 25 | Avocado | 4.7 | 14.9 | 17.3 | PBT-Eco-2 | 26.8 | 18.8 | PET (5018) | 47.3 | 19.8 | 0 | 0.8 |
| 26 | Avocado | 6.1 | 15.0 | 17.3 | PBT- Eco-2 | 34.7 | 18.8 | PET (5018) | 40.8 | 19.8 | 0 | 0.8 |
| 27 | Mix-1 | 5.4 | 15.0 | 17.3 | PBT-Eco | 30.6 | 18.8 | PET (5018) | 43.1 | 19.8 | 0 | 0.7 |
| 28 | Mix-2 | 5.4 | 15.0 | 17.3 | PBT-Eco | 30.6 | 18.8 | PET (5018) | 43.1 | 19.8 | 0 | 0.7 |
| 29 | Mix-2 | 5.4 | 15.0 | 17.3 | PBT-Eco | 30.6 | 18.8 | PET (5018) | 43.1 | 19.8 | 0 | 0.7 |
| 30 | Mix-3 | 5.4 | 15.0 | 17.29 | PBT-Eco | 30.6 | 18.8 | PET (5018) | 43.1 | 19.8 | 0 | 0.7 |
| 31 | Mix-4 | 5.4 | 15.0 | 17.29 | PBT-Eco | 30.6 | 18.8 | PET (5018) | 43.1 | 19.8 | 0 | 0.7 |
| 32 | Mix-5 | 5.4 | 15.0 | 17.29 | PBT-Eco | 30.6 | 18.8 | PET (5018) | 43.1 | 19.8 | 0 | 0.7 |
| C_7 | Avocado | 6.9 | 20.8 | 17.3 | PBT-Eco | 26.2 | 18.8 | PBT | 46.2 | 19.3 | 0 | 0.7 |
| C_8 | Avocado | 13.3 | 32.5 | 17.3 | PBT-Eco-3 | 27.6 | 18.8 | PET(5018) | 40.8 | 19.8 | 0 | 0.8 |

| Experiment no | Carbon wt % | Glass 3B wt % | (δsub − δP1)² (J/cm³) | Release at 200° C. [mg] 1st treatment | 5th treatment | E-mod at 200° C. MPa |
|---|---|---|---|---|---|---|
| 18 | 15[3)] | 0 | 4.5 | 1.8 | 0.3 | 124 |
| 19 | 15[4)] | 0 | 4.5 | 1.4 | 0.3 | 119 |
| 20 | 22.7[3)] | 9.1 | 4.5 | 1.6 | 0.4 | 404 |
| 21 | 22.7[4)] | 9.1 | 4.5 | 2.0 | 0.4 | 431 |
| 22 | 10[3)] | 0 | 1.8 | 0.8 | 0.1 | 151 |
| 23 | 20.3[1)] | 0 | 2.2 | 0.5 | 0.2 | 610 |
| 24 | 18.4[1)] | 0 | 2.2 | 1.1 | 0.1 | 398 |
| 25 | 20.3[1)] | 0 | 2.2 | 0.7 | 0.2 | nd |
| 26 | 17.5[1)] | 0 | 2.2 | 0.8 | 0.2 | nd |
| 27 | 20.2[2)] | 0 | 2.1 | 0.7 | 0.1 | 431 |

TABLE 6-continued

Experiments with two polymers and quantification of E-modulus

| | | | | | | |
|---|---|---|---|---|---|---|
| 28 | 20.2[2)] | 0 | 2.1 | 0.5 | 0.2 | 353 |
| 29 | 20.2[1)] | 0 | 2.1 | 0.4 | 0.1 | 309 |
| 30 | 20.2[1)] | 0 | 2.1 | 0.4 | nd | nd |
| 31 | 20.2[1)] | 0 | 2.1 | 0.3 | nd | nd |
| 32 | 20.2[1)] | 0 | 2.1 | 0.5 | nd | nd |
| C_7 | 20.0[1)] | 0 | 2.2 | nd | nd | No thermal intregrity |
| C_8 | 17.5[1)] | 0 | 2.2 | nd | nd | No thermal intregrity |

Sub Mix-1 = 95 wt % avocado/5 wt % argan oil
Sub Mix-2 = 95 wt % avocado/2.5 wt % argan/2.5 wt % camealia oil
Sub Mix-3 = 95 wt % avocado/2.5 wt % argan/2.5 wt % macadamia nut oil
Sub Mix-4 = 95 wt % avocado/2.5 wt % argan/2.5 wt % safflower oil
Sub Mix-5 = 95 wt % avocado/2.5 wt % argan/2.5 wt % apricot kernel oil
Carbon[1)] = Expanded Graphite (C-Therm 01)
Carbon[2)] = 99.25 wt % Expanded Graphite (C-Therm 01) and 0.75 wt % Carbon Black (Black pearls 800)
Carbon[3)] = Graphite (Ecophit GFG1200)
Carbon[4)] = 95 wt % Graphite (Ecophit GFG1200) and 5 wt % Carbon black (Timcal Ensaco260G)

Table 3 clearly shows that with polymer compositions having a Δ in the range from 0.5 to 24, release of thermo-releasable substance was visible on the plaque and the release could be quantified and was above 0. For polymer compositions with Δ above 24, no release was visible and no release could be measured.

Experiments 5 to 9 in table 4 all showed sufficient thermal stability at 200° C., which indicates that these compositions were suitable for high-heat application. Comparative example C-5 showed no sufficient thermal stability, which indicated that this composition was not suitable for high-heat application, and also indicates that the E-modulus of comparative example C-5 cannot reach 50 MPa at 200° C.

Moreover, table 4 shows that with a polymer composition having a Δ in the range from 0.5 to 24, but no thermal stability, release at 200° C. could not be measured more than once as these plates did not have sufficient mechanical integrity, and this also means that the E-modulus cannot reach 50 MPa at 200° C.

Table 5 shows in experiments 10 to 17 polymer compositions having a Δ in the range from 0.5 to 24.0 in which release was visible. Comparative example C_6 shows that with a Δ below 0.5 no release of thermo-releasable substance was visible.

Table 6 shows examples for which the E-modulus was quantified at 200° C. For examples 30 to 32 E-modulus was not measured, but they are expected to are similar to examples 27 to 29, as the same polymers were employed in the same amounts.

For comparative examples C_7 and C_8 the thermal stability was so low, that no E-modulus could be measured at 200° C. The dog bone bars of these examples broke in the clamp at the start of the tensile experiment, and no release at 200° C. could be measured as these plates did not have sufficient mechanical integrity.

The invention claimed is:

1. A polymer composition suitable for high-heat application comprising a melt-blend mixture of:
   (a) at least one polymer 1 having a solubility parameter $\delta P1$;
   (b) a thermo-releasable substance having a solubility parameter $\delta sub$ which is a liquid at 200° C., wherein the thermo-releasable substance is mixed with the at least one polymer 1 in an amount which is at least 0.1 wt % based on total weight of the composition and in an amount which is in a range from 0.5 wt % to 70 wt % based on weight of the polymer 1; wherein
   the composition exhibits a $\Delta=(\delta sub-\delta P1)^2$ which is in a range from 0.5 to 24.0 and has an E-modulus measured according to method ISO 527-1 at 200° C. of at least 50 MPa.

2. The polymer composition according to claim 1, wherein Δ is in the range from 1.0 to 20.0.

3. The polymer composition according to claim 1, wherein the E-modulus of the composition is at least 70 MPa at 200° C. measured according to method ISO 527-1.

4. The polymer composition according to claim 1, wherein the E-modulus of the composition is at least 90 MPa at 200° C. measured according to method ISO 527-1.

5. The polymer composition according to claim 1, wherein the amount of thermo-releasable substance is present in the range from 0.5 wt % to 30 wt % based on the total weight of the composition.

6. The polymer composition according to claim 1, wherein the thermo-releasable substance is selected from the group consisting of polydimethylsiloxane, linear parafins, natural oils and combinations thereof.

7. The polymer composition according to claim 1, wherein the thermo-releasable substance comprises a natural oil selected from the group consisting of avocado oil, argan oil, camealia oil, sunflower oil, macadamia nut oil, safflower oil, apricot kernel oil and combinations thereof.

8. The polymer composition according to claim 1, wherein the polymer 1 is at least one selected from the group consisting of thermoplastic polyesters, syndiotactic polystyrene, styrene maleic anhydride copolymers, polybutylene naphthalate and polyamides.

9. The polymer composition according to claim 1, wherein the composition further comprises a semi-crystalline polymer with a melting temperature of at least 10° C. above an application temperature, which is selected from the group consisting of polyethylene terephthalate, polyamides, polystyrenes, polybutylene naphthalate (PBN) and polyethylene naphthalate (PEN).

10. The polymer composition according to claim 9, wherein the polymer 1 is a polybutylene terephthalate-co-dimer fatty acid and the thermo-releasable substance comprises a natural oil selected from the group consisting of avocado oil, argan oil, camealia oil, sunflower oil and combinations thereof.

11. The polymer composition according to claim 1, wherein the polymer 1 is a polybutylene terephthalate-co-dimer fatty acid and the thermo-releasable substance comprises a natural oil selected from the group consisting of avocado oil, argan oil, camealia oil, sunflower oil and combinations thereof and the further polymer is polyethyleneterephthalate.

12. The polymer composition according to claim 1, wherein Δ is in the range from 1.0 to 15.0.

13. The polymer composition according to claim 1, wherein Δ is in the range from 1.0 to 10.0.

14. A personal care device comprising a surface for contacting hair, wherein the surface of the device is made from the polymer composition according to claim 1.

15. The personal care device according to claim 14, wherein the surface for contacting hair is operated at a temperature of at least 100° C.

16. The personal care device according to claim 14, wherein the device is a hair-straightener.

17. A hair-straightener comprising a sleeve made from the polymer composition according to claim 1.

* * * * *